(12) United States Patent
Steinhardt et al.

(10) Patent No.: US 9,216,081 B2
(45) Date of Patent: Dec. 22, 2015

(54) MODULAR TOTAL PROSTHESIS FOR THE MIDDLE EAR

(75) Inventors: Uwe Steinhardt, Hirrlingen (DE); Heinz Kurz, Dusslingen (DE); Georg Schmid, Tuebingen (DE); Walter Heckmann, Rottenburg (DE)

(73) Assignee: HEINZ KURZ GMBH MEDIZINTECHNIK, Dusslingen (DE)

( * ) Notice: Subject to any disclaimer, the term of this patent is extended or adjusted under 35 U.S.C. 154(b) by 807 days.

(21) Appl. No.: 12/313,388

(22) Filed: Nov. 20, 2008

(65) Prior Publication Data

US 2009/0164010 A1 Jun. 25, 2009

(30) Foreign Application Priority Data

Dec. 21, 2007 (DE) .......................... 10 2007 062 151

(51) Int. Cl.
*A61F 2/18* (2006.01)
(52) U.S. Cl.
CPC ............. *A61F 2/18* (2013.01); *A61F 2002/183* (2013.01)
(58) Field of Classification Search
CPC .............................. A61F 2/18; A61F 2002/183
USPC ........................................................... 623/10
See application file for complete search history.

(56) References Cited

U.S. PATENT DOCUMENTS

| 4,601,723 | A | * | 7/1986 | McGrew | 623/10 |
| 4,728,333 | A | * | 3/1988 | Masse et al. | 623/23.28 |
| 5,180,391 | A | * | 1/1993 | Beoni | 623/10 |

(Continued)

FOREIGN PATENT DOCUMENTS

| DE | 299 04 770 U1 | 7/1999 |
| DE | 200 14 659 U1 | 1/2001 |

(Continued)

OTHER PUBLICATIONS

Essentials of Audiology by Stanley A Gelfand, third edition, 2009, Thieme Medical Publishers, p. 42.*

(Continued)

*Primary Examiner* — Jacqueline Woznicki
(74) *Attorney, Agent, or Firm* — Flynn, Thiel, Boutell & Tanis, P.C.

(57) ABSTRACT

A total prosthesis for the middle ear, with a prosthesis body, with a first coupling element for connection of the prosthesis to the tympanic membrane or for coupling to the manubrium, and with a second coupling element for connection to the footplate of the stirrup, which second coupling element has a receiving part, connected rigidly to the prosthesis body, and has an insert part with a plug element that can be inserted coaxially, and with a shoe that is connected rigidly to the plug element and that bears on the footplate of the stirrup, is characterized in that the receiving part has an elongate cavity as a receiving opening with a cylindrical bore which extends axially and encloses the full circumference of the plug element and whose inside diameter is greater than the maximum transverse extent of the plug element, which elongate cavity is closed at the end away from the insert part and acts as an end abutment for the plug element, and in that the second coupling element extends axially by at most a third of the axial length of the prosthesis body. In this way, it is easy to produce a desired defined length of the prosthesis, which also remains fixed after surgery, and it is also possible, during surgery, to react to the specific individual situation of the stirrup bone.

19 Claims, 6 Drawing Sheets

(56) References Cited

U.S. PATENT DOCUMENTS

| | | | |
|---|---|---|---|
| 6,168,625 B1 * | 1/2001 | Prescott | 623/10 |
| 6,432,139 B1 | 8/2002 | Elies et al. | |
| 6,554,861 B2 | 4/2003 | Knox et al. | |
| 6,579,317 B2 | 6/2003 | Kurz | |
| 7,204,850 B2 * | 4/2007 | Steinhardt et al. | 623/10 |
| 2002/0045939 A1 | 4/2002 | Kurz | |

FOREIGN PATENT DOCUMENTS

| | | |
|---|---|---|
| DE | 203 10 609 U1 | 10/2003 |
| DE | 20 2004 012 148 U1 | 1/2005 |
| DE | 20 2007 012 217 U1 | 1/2008 |
| EP | 1 181 907 B1 | 5/2004 |
| WO | WO 99/42060 A | 8/1999 |
| WO | WO 02/069850 A1 | 9/2002 |

OTHER PUBLICATIONS

European Search Report dated Dec. 3, 2008.
German Office Action dated Jun. 5, 2008.

* cited by examiner

MODULAR TOTAL PROSTHESIS FOR THE MIDDLE EAR

BACKGROUND OF THE INVENTION

The invention relates to a middle ear prosthesis for total reconstruction of the ossicular chain in humans, with a shaft-like prosthesis body which at one end has a first coupling element designed either as a head plate for mechanical connection of the prosthesis to the tympanic membrane or as a clip for coupling the prosthesis to the manubrium, and which at the other end has a second coupling element for mechanical connection of the prosthesis to the footplate of the stirrup, which second coupling element has a receiving part, connected rigidly to the prosthesis body, and an insert part with a plug element that can be inserted into the receiving part coaxially with respect to the longitudinal axis of the shaft-like prosthesis body, and with a shoe that is connected rigidly to the plug element and that bears on the footplate of the stirrup in the implanted state of the prosthesis.

In the design with a head plate for bearing on the tympanic membrane, a total prosthesis of this kind is known from EP 1 181 907 B1.

DE 299 04 770 U1 also describes middle ear prostheses that are designed to be fitted between the tympanic membrane and the footplate of the stirrup. In these known prostheses, however, the second coupling element for mechanical connection to the footplate of the stirrup does not comprise a receiving part or an insert part. Instead, a receiving part is provided at the end of a first shaft portion just behind the first coupling element designed as a head plate for bearing on the tympanic membrane. A plug element protruding from a contiguous second shaft portion can be inserted into this receiving part in order to connect the first shaft portion to the second shaft portion, at the other end of which a second coupling element, in the form of a shoe for bearing on the footplate of the stirrup, is integrally mounted.

DE 20 2004 012 148 U1 describes a middle ear implant which has, at one end, a first coupling element for the manubrium or tympanic membrane and, at the other end, a second coupling element in the form of a prosthesis base with a prosthesis shoe plate for connection to the footplate of the stirrup. The connection part between the two coupling elements, which is formed by a rod-shaped prosthesis shaft in most other middle ear prostheses according to the prior art, is here intended to be "conically micro-slit", such that two elongate branches, in part conical and in part parallel, extend away from the first coupling element, at a distance from each other, in the direction of the second coupling element. A ball is intended to be fitted into the gap between the two branches, said ball being rigidly connected to the top face of the prosthesis shoe plate directed away from the footplate of the stirrup. A sleeve engaged over the conical part of the two branches is intended to press together the two branches and the ball between them. This is intended to achieve an articulated coupling of the prosthesis base to the connection part between the two coupling elements.

A design of the first coupling element of a middle ear prosthesis as a clip for coupling to the manubrium is already known per se, for example from DE 203 10 609 U1. However, the prostheses described therein do not have a second element designed as a shoe for bearing on the footplate of the stirrup, but instead have either a plunger, for direct connection to the inner ear, or a second clip.

DE 20 2007 012 217 U1 in turn describes middle ear prostheses with a second coupling element designed as a shoe for mechanical connection to the footplate of the stirrup. The first coupling element described therein can also be designed as a clip for securing the prosthesis to another member of the auditory ossicle chain, although not to the manubrium, but instead to the process of the anvil, for example. Moreover, the second coupling element designed as a shoe is not rigidly connected to a plug element insertable into a receiving part.

The role of the middle ear in humans, with its auditory ossicles, is to take up the sound waves impacting the tympanic membrane via the external acoustic meatus and transmit them to the fluid-filled inner ear. The three auditory ossicles are the hammer (malleus), which is attached to the tympanic membrane, the stirrup (stapes), which is connected via its footplate (basis stapedis) to the inner ear, and the anvil (incus), which is situated between the hammer and the stirrup and is connected to these in an articulated manner. Otosclerosis, for example, is a disease of the human petrous bone (the bone in which the whole ear sits) in which inflammatory-like transformation processes affecting the bone may lead to a fixing of the normally loosely oscillating stirrup. As a result of this, the sound signal is not transmitted, or is transmitted only incompletely, to the inner ear via the ossicular chain, and this leads to impaired hearing.

Middle ear prostheses are used to improve the sound transmission in various pathological conditions. They are used to transmit the sound from the tympanic membrane to the inner ear in cases where the auditory ossicles of the human middle ear are completely or partially absent or damaged. Three types of middle ear prostheses that are used particularly frequently are the stirrup prostheses, partial prostheses and total prostheses. Stirrup prostheses (stapes prostheses) are fixed to the anvil and protrude via a piston into the inner ear. Partial prostheses in most cases lie with a head plate on the tympanic membrane and establish a connection to the head of the stirrup. Total prostheses connect the tympanic membrane to the footplate of the stirrup. The present invention relates exclusively to total prostheses.

An important problem arising in every reconstruction of the auditory ossicle chain in humans lies in the choice of the correct prosthesis length. For anatomical reasons, the required lengths vary within a range of several millimeters. Consequently, in the surgical implantation of a middle ear prosthesis, either a sufficiently wide choice of prostheses of different axial lengths must be kept available or the ossicular prostheses used must be able to be brought, during surgery, from a maximum or minimum starting length to the required final axial length.

Another serious problem particularly of total prostheses is that, in cases where the anvil is absent and the superstructure of the stirrup is absent at the same time, ossicle reconstructions always carry a high inherent risk of instability or dislocation of the prosthesis. In addition, individual patients present different anatomical situations, which cannot generally be clearly established prior to surgery and which not only concern the required axial length of the prosthesis but also numerous other geometric parameters. These make it difficult for the operating surgeon to achieve a lasting optimal connection between the prosthesis and the footplate of the stirrup.

SUMMARY OF THE INVENTION

The object of the present invention is, by contrast, to improve the generic middle ear prosthesis of the type described at the outset and to do so by the simplest possible technical means, in such a way that, on the one hand, a desired defined length of the prosthesis can be easily established even before it is fitted between the two attachment points, this length also remaining fixed after completion of the operation, and, on the other hand, it is possible to react specifically, during the operation, to the individual situation of the stirrup (or of the remnants thereof) presented by the patient and to achieve an optimal geometric coupling of the prosthesis to the footplate of the stirrup without having to keep a large number of differently configured middle ear prostheses in stock.

According to the invention, this object is achieved in a surprisingly simple and effective way by virtue of the fact that the receiving part, at its end directed away from the prosthesis body, has a receiving opening designed as an elongate cavity with a cylindrical bore which extends in the axial direction of the prosthesis body and encloses the full circumference of the plug element of the insert part, that the inside diameter of the elongate cavity is greater than the maximum transverse extent of the plug element transverse to the longitudinal axis of the shaft-like prosthesis body, that the elongate cavity is closed at the end directed away from the insert part and, in the assembled state, acts as an end abutment for the plug element, and that the second coupling element extends, in the axial direction of the prosthesis, by at most a third of the axial length of the prosthesis body.

In this way, depending on the individual situation surrounding the patient's stirrup bone during the operation, it is possible to establish an optimal implant situation adapted exactly to the patient simply by pushing the plug element of an insert part of suitable axial length and with a geometrically optimal shoe into the elongate cavity of the receiving part of the prosthesis.

In this connection, it is particularly useful that the individual adaptation does not require stocking a large assortment of prostheses of different lengths and keeping them to hand during each operation. Instead, a uniform standard prosthesis with head plate, shaft and receiving part can be used which, as has been described above, is adapted optimally to the particular individual by simple fitting of an insert part selected from an assortment of insert parts.

This permits, in a simple and inexpensive way, almost any desired variation of the length, and optimal adaptation of the geometry, of the middle ear prosthesis in situ during surgery. The adjustment of the desired individual prosthesis length and geometry, and therefore the handling of the prosthesis, are particularly simple.

Undesired subsequent changes to the length and/or position of the prosthesis after surgery are reliably avoided by the optimal adaptation made possible according to the invention.

An embodiment of the middle ear prosthesis is very particularly preferred in which the second coupling element extends, in the axial direction of the prosthesis, by at most a quarter of the axial length of the prosthesis body, such that it is possible in particular to reliably avoid a buckling of the prosthesis when fitting the stirrup side end portion by coupling the insert part in the receiving part.

In one category of embodiments of the invention, the insert part can be actively wedged to the receiving part at selectable discrete relative coaxial positions along an axial extent by means of an external action on the insert part and/or on the receiving part, such that almost any desired prosthesis length below the maximum length defined by the basic design of the prosthesis can be precisely adopted on an individual basis.

In simple developments of these embodiments, the insert part can be wedged by the action of an external mechanical force, in particular by means of a crimping tool acting in the radial direction on the receiving part.

In more refined embodiments, which are also slightly more complicated to produce however, the insert part can be actively wedged to the receiving part by external application of heat to the middle ear prosthesis, in particular by heating the middle ear prosthesis to body temperature.

Variants of these developments are very particularly advantageous in which the insert part and/or the receiving part are made completely or partially of a material with shape memory (memory effect), in particular of nitinol or a polymer. The use of such materials is known per se in the field of middle ear prostheses but has proven particularly effective specifically in connection with the present invention.

For reasons relating to manufacturing technology, embodiments of the middle ear prosthesis according to the invention are to be preferred in which the plug element has a continuously cylindrical shape.

A geometrically and ergonomically expedient embodiment of the middle ear prosthesis according to the invention is characterized in that the plug element, at its axial end directed toward the receiving part in the assembled state, has a thickened area. This also permits particularly good coupling of the insert part in the receiving part.

In practice, developments of this embodiment prove effective in which the thickened area of the plug element is in the shape of an ellipsoid, in particular an ellipsoid of revolution, preferably a sphere. These geometries do not cause any great problems in terms of manufacturing.

In this way, the second coupling element can be easily designed as a ball joint, which has the advantages described further below.

Receiving parts are particularly easy to produce which, in their cross section perpendicular to their longitudinal axis, have a cylindrical outer contour. However, in addition to circular cylindrical shapes, it is also possible to have receiving parts with a rectangular cross section.

After the prosthesis has been placed surgically in the middle ear and the tympanic membrane has been closed again, the so-called incorporation phase starts. During this period, scars form and generate unpredictable forces, which can lead to the prosthesis shifting from its local position. In the case of a stiff connection between head plate and shaft, elevated pressure peaks can arise between the edge of the head plate and the tympanic membrane or transplant between tympanic membrane and head plate. These peaks can be so high as to result in penetration or extrusion through the tympanic membrane. For this reason, it is very useful if, after surgery, the prosthesis has a certain degree of mobility, such that the head plate can automatically adjust to the position of the tympanic membrane after the operation. Since the anatomical features of the ear, for example the position, shape and size of the stirrup, anvil, hammer and tympanic membrane, also vary between individuals, it is very advantageous if middle ear prostheses are not made rigid, but instead have a certain flexibility or variability.

In the auditory ossicle prosthesis according to the invention, the connection element between the two securing elements is generally designed as an elongate shaft, as is well known per se from the prior art. In order to achieve the abovementioned flexibility or variability of the prosthesis, as described in detail in EP 1 181 907 B1 for example, it is possible, in a particularly preferred embodiment of the invention, to provide a joint, in particular a ball joint.

With a view to particularly good postoperative mobility of the prosthesis, developments are advantageous in which the prosthesis body has a large number of further rotary elements adjoining one another, preferably an axially extending ball joint chain.

The middle ear prosthesis according to the invention, or parts thereof, can be made of titanium and/or gold and/or tantalum and/or steel and/or of an alloy of said metals. In addition to its strength and excellent sound conduction properties, titanium in particular is also known to have excellent biocompatibility in the middle ear of humans.

In respect of the abovementioned postoperative change of position, embodiments of the invention are advantageous in which the prosthesis, or parts thereof, in particular one of the securing elements, is/are made of a material with shape memory (memory effect) or superelastic properties, preferably of nitinol or a polymer, which is known per se from, for example, WO 02/069850 A1 or U.S. Pat. No. 6,554,861 B2.

Alternatively or in addition to this, parts of the middle ear prosthesis in other embodiments according to the invention can be made of a ceramic material.

However, embodiments of the invention are also possible in which the entire prosthesis or parts thereof is/are made of biocompatible plastics, in particular silicone, polytetrafluoroethylene (PTFE) or composite fiber materials, in particular carbon fibers or a thermoplastic. With these materials, postoperative rejection reactions can in most cases also be prevented.

In addition to the post-operative change of position, a further problem also arises after implantation of middle ear prostheses. This is due to the fact that the middle ear of the human body constitutes a "semi-open bearing". Any implantation material introduced into the body, in the context of a reconstruction of the middle ear and of its structures, is therefore subject to a particular stress arising from the fact that it lies in a contaminated and infected environment, which generally attacks the material. Since the aim of implanting a middle ear prosthesis must be that the implant remains in the patient's middle ear for as long as possible and without complications, a protracted attack on the material can lead to damage of the prosthesis and/or to local infection. Both consequences are unacceptable. To prevent damage of the implanted material and also of the surrounding tissue on a permanent basis, another particularly preferred embodiment of the invention involves a biologically active coating, in particular a coating that inhibits growth and/or promotes growth and/or has an antibacterial action, being provided at least in some areas of the surface of the middle ear prosthesis. The head plate of the middle ear prosthesis according to the invention should in principle have a coating that promotes growth.

An embodiment of the middle ear prosthesis according to the invention is particularly preferred in which the weight distribution of the individual parts of the prosthesis is calculated as a function of a desired, predefinable frequency response of the sound conduction in the middle ear. It is thus possible, without major additional technical outlay, to achieve a degree of tuning of the sound propagation properties by means of an individually configured middle ear prosthesis.

For example, such a tuning effect can be achieved, in particular embodiments, by the fact that at least one additional weight is secured on a part of the ossicular chain or of the prosthesis as a function of a desired, predefinable frequency response of the sound conduction in the middle ear. In advantageous developments of these embodiments, the additional weight is secured on a part of the ossicular chain or the prosthesis by means of a clip. In addition, the additional weight and/or the clip can also be coated with a biologically active coating.

The scope of the present invention also includes a group of middle ear prostheses, of the above-described type according to the invention with an insert part for insertion into the receiving part, in which the shoe, which is rigidly connected to the plug element and bears on the footplate of the stirrup in the implanted state of the prosthesis, has a plate-shaped or stamp-shaped structure.

A preferred category of embodiments is characterized in that the end portion of the shoe bearing on the footplate of the stirrup in the implanted state of the middle ear prosthesis has a surface curved concavely in the direction of the plug element, which generally ensures the best hold of the prosthesis on the footplate of the stirrup.

For other individual geometries of the stirrup remnants that are found in the patient, the use of an alternative category of embodiments may be favorable in which the end portion of the shoe bearing on the footplate of the stirrup in the implanted state of the middle ear prosthesis is flat and bears over a large surface area.

Another category of insert parts for special purposes is characterized in that the end portion of the shoe bearing on the footplate of the stirrup in the implanted state of the middle ear prosthesis has a surface curved convexly in the direction away from the plug element and thus permits a punctiform contact.

In preferred developments of this category of insert parts, the end portion of the shoe has the shape of an ellipsoid of revolution, preferably a spherical shape, which is relatively easy to produce.

For better securing of the insert part on the stirrup, it is possible, in further developments, for the end portion of the shoe to have a tip directed toward the footplate of the stirrup in the implanted state of the middle ear prosthesis, which allows the shoe to drill into the footplate of the stirrup and achieves greater adherence through increased friction.

Developments often prove advantageous in which the shoe, on its outer circumference, has radially outwardly protruding stabilizer wings, which among other things permit centering of the arrangement in the oval recess of the footplate of the stirrup.

Alternatively, in further developments of the insert part according to the invention, the outer circumference of the shoe can have radially inwardly extending recesses into which bone remnants of the individual patient's stirrup engage and thus permit a secure hold of the prosthesis.

In other individual situations, a geometry of the insert part may also be expedient in which the shoe has a smaller maximum outer circumference than the plug element. This permits simple reduction of the diameter and, consequently, of the effective contact surface of the shoe on the footplate of the stirrup.

For hygiene reasons, it is generally highly recommended that, before being inserted into the receiving part, the insert part is stored in a sterile, preferably airtight package.

The scope of the present invention also includes a middle ear prosthesis in which an assortment of insert parts designed according to the invention is provided, where the insert parts are present in different geometric configurations but are designed in such a way that the middle ear prosthesis has the same axial overall length after the respective plug element of an insert part has been inserted as far as the end abutment into the elongate cavity of the receiving part.

In this connection, an embodiment is advantageous which is characterized in that, after the plug element has been inserted as far as the end abutment into the elongate cavity of the receiving part, the overall length of the middle ear prosthesis is between 0.3 mm and 0.8 mm, preferably 0.5 mm. The insert parts will particularly preferably be designed such that, although they have different geometries, they each lead to the same axial length of the middle ear prosthesis when they are inserted in the receiving part.

Further features and advantages of the invention will become clear from the following detailed description of illustrative embodiments of the invention, from the figures in the drawing, which shows important details of the invention, and also from the claims. The individual features can each be realized singly or in any desired combinations in variants of the invention.

Illustrative embodiments of the invention are explained in more detail in the following description and are depicted in the schematic drawing.

DESCRIPTION OF THE PREFERRED EMBODIMENTS

Figure 1:
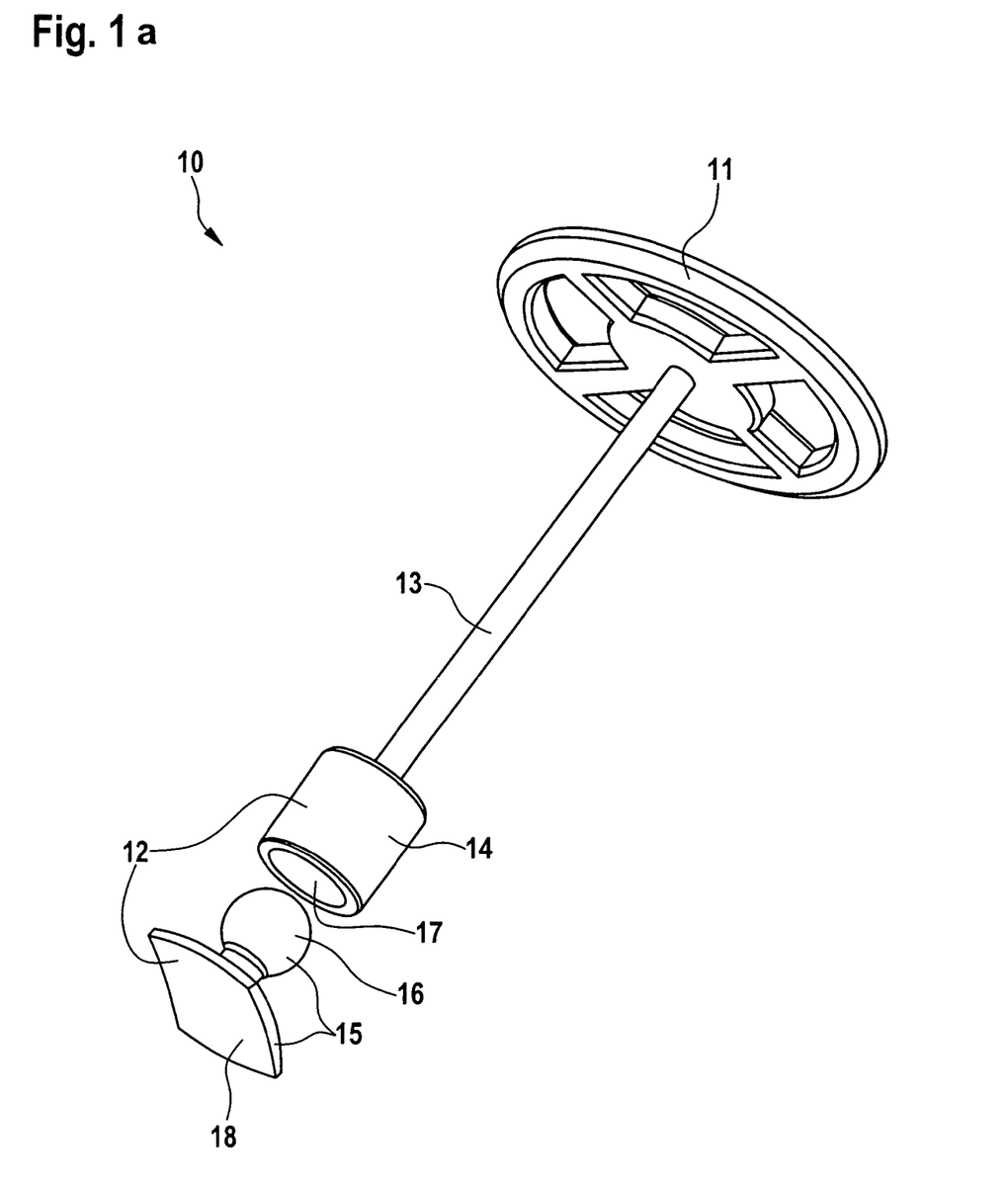
FIG. 1a shows a schematic perspective view of a first embodiment of the middle ear prosthesis according to the invention, with a tympanic membrane head plate as first securing element.
FIG. 1b shows a schematic section through the embodiment according to FIG. 1a, in its postoperative situation when fitted in the middle ear.
Figure 1B:
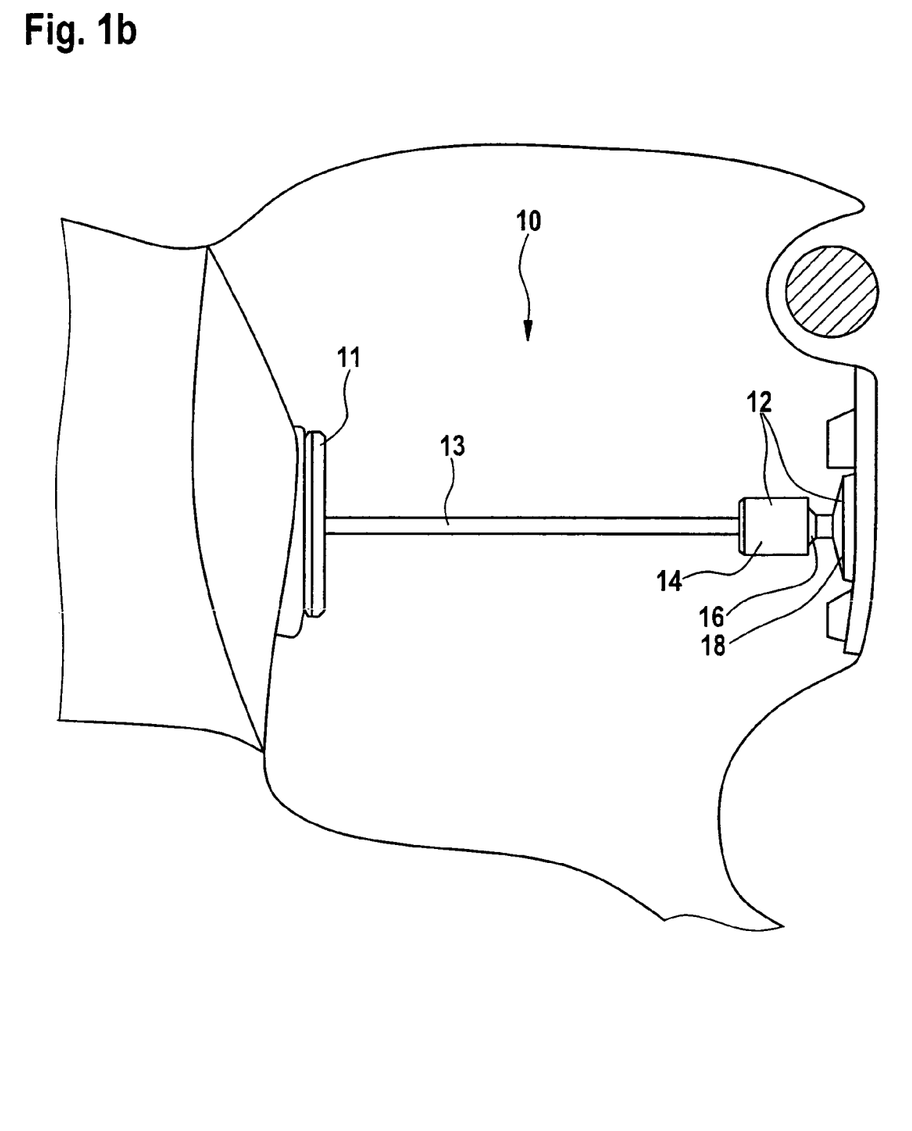
Figure 2:
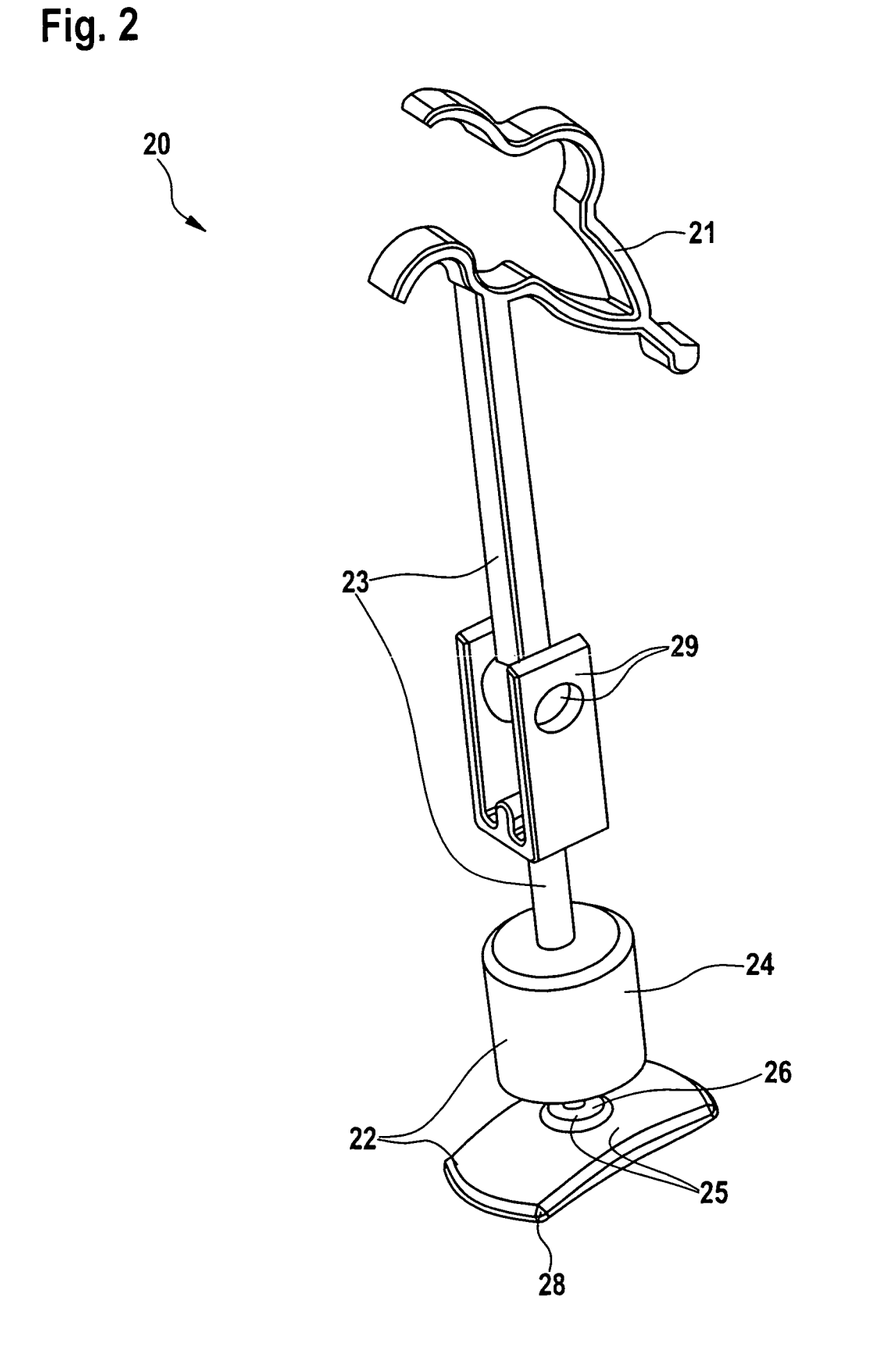
FIG. 2 shows an embodiment with a clip as first securing element, and with a ball joint in the prosthesis body.

The embodiments of the middle ear prosthesis 10; 20 according to the invention, shown schematically in FIGS. 1a, 1b and 2, differ in some design details and in each case have, at one of their ends, a first securing element 11; 21.

The securing element 11 in FIGS. 1a and 1b is designed as a head plate for applying the prosthesis to the tympanic membrane, and the securing element 21 in FIG. 2 is in the form of a clip for mechanical connection to the manubrium.

At the other end of the middle ear prosthesis 10; 20, there is in each case a second securing element 12; 22 for mechanical coupling of the prosthesis to the footplate of the stirrup. Arranged between these securing elements, there is a prosthesis body 13; 23 that is designed as an elongate shaft and that connects the two securing elements 11; 21 and 12; 22 to each other in a sound-conducting manner.

The second securing element 12; 22 in each case comprises a first piece designed as a receiving part 14; 24 and connected rigidly to the prosthesis body 13; 23, and a second piece which is designed as an insert part 15; 25 and which has a plug element 16; 26 that can be inserted into a receiving opening of the receiving part 14; 24 coaxially with respect to the longitudinal axis of the prosthesis body 13; 23, and has a shoe 18; 28 that is connected rigidly to the plug element 16; 26 and bears on the footplate of the stirrup in the implanted state of the prosthesis 10; 20.

According to the invention, the receiving part 14; 24, at its end directed away from the prosthesis body 13; 23, has in each case a receiving opening designed as an elongate cavity 17 with a cylindrical bore which extends in the axial direction of the prosthesis body 13; 23 and encloses the full circumference of the plug element 16; 26 of the insert part 15; 25 in the assembled state. The inside diameter of the elongate cavity 17 is greater than the maximum transverse extent of the plug element 16; 26 transverse to the longitudinal axis of the shaft-like prosthesis body 13; 23. The elongate cavity 17 is closed at the end directed away from the insert part 15; 25 and, in the assembled state, acts as an end abutment for the plug element 16; 26. The second coupling element 12; 22 extends, in the axial direction of the prosthesis, by at most a third, preferably at most a quarter, of the axial length of the prosthesis body 13; 23.

In the embodiment according to FIG. 2, a ball joint 29 is integrated into the prosthesis body 23 in order to achieve a degree of postoperative flexibility of the middle ear prosthesis 20 between its connection points.

The weight distribution of the individual parts of the middle ear prosthesis 10; 20 according to the invention can be calculated, as a function of a desired and predefinable frequency characteristic of the sound conduction in the middle ear, so as to permit individual tuning of the sound conduction properties.

At least some parts of the middle ear prosthesis 10; 20 can be provided with a biologically active coating, in particular a coating that inhibits growth and/or a coating that promotes growth and/or an antimicrobial coating.

In the embodiments according to FIGS. 3a to 3f, the insert parts 35a; 35b; 35c; 35d; 35e; 35f each have different geometric configurations which, as has been explained above, permit optimal adaptation of the middle ear prosthesis to the different individual situations that are found between patients in the area of the footplate of the stirrup.

Figure 3A:
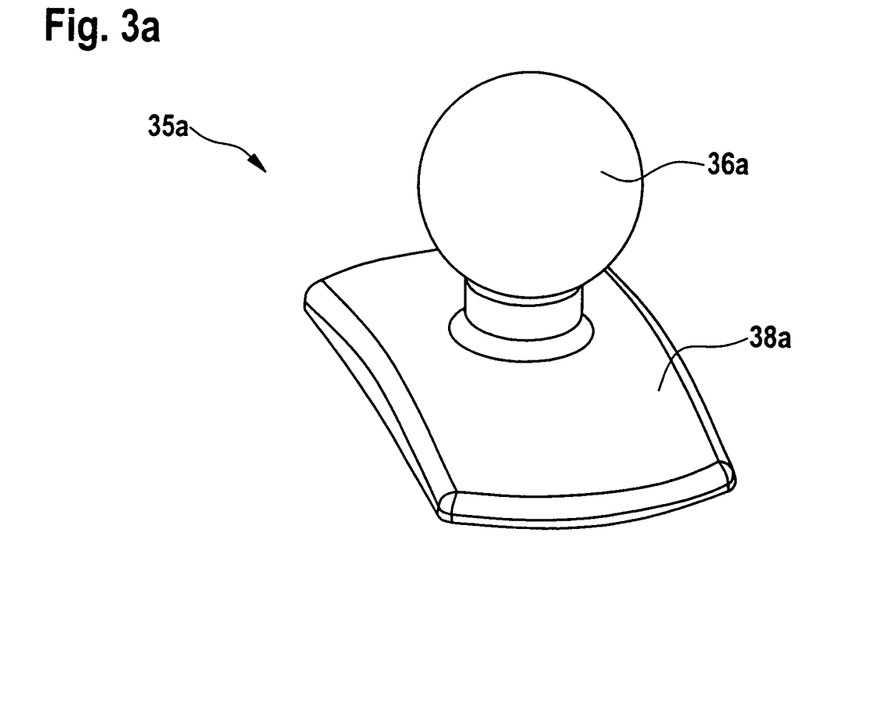
FIGS. 3a-f show various embodiments of the insert part according to the invention that differ in terms of their geometry and function.

The insert part 35a has a spherically thickened plug element 36a and a concavely curved shoe 38a.

Figure 3B:
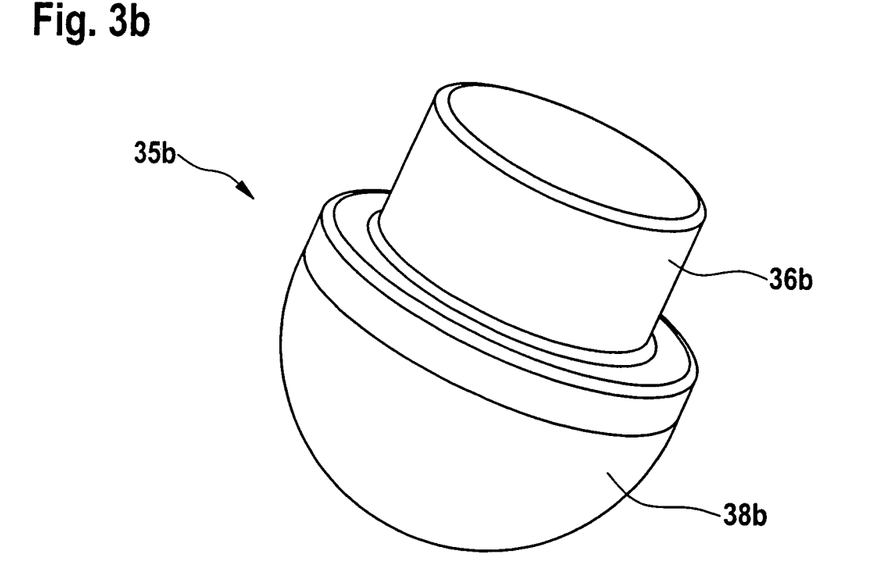

The insert part 35b comprises a cylindrical plug element 36b, and a shoe 38b curved convexly outward in a sphere shape.

Figure 3C:
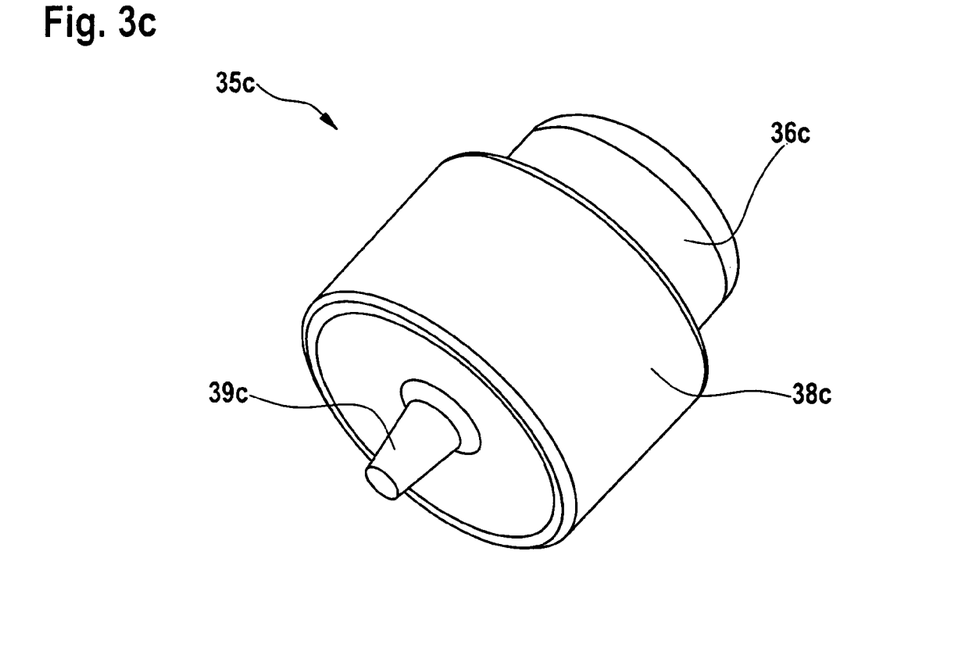
Figure 3D:
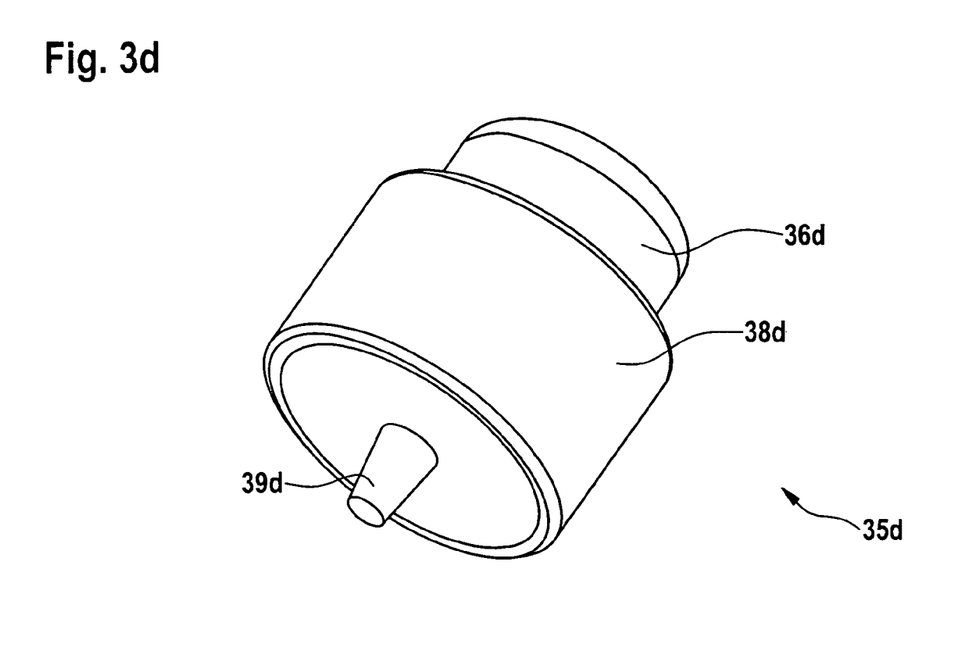

The insert parts 35c; 35d each have a substantially cylindrical plug element 36c; 36d, and a flat shoe 38c; 38d which, on its end portion, in each case has a tip 39c; 39d directed toward the footplate of the stirrup in the implanted state of the middle ear prosthesis, which end portion can be flat, concave or also convex. In the area of its attachment to the end portion of the shoe 38c, the tip 39c in FIG. 3c is additionally surrounded by an annular bead, which prevents the end portion from bearing over a large surface area on the footplate of the stirrup.

Figure 3E:
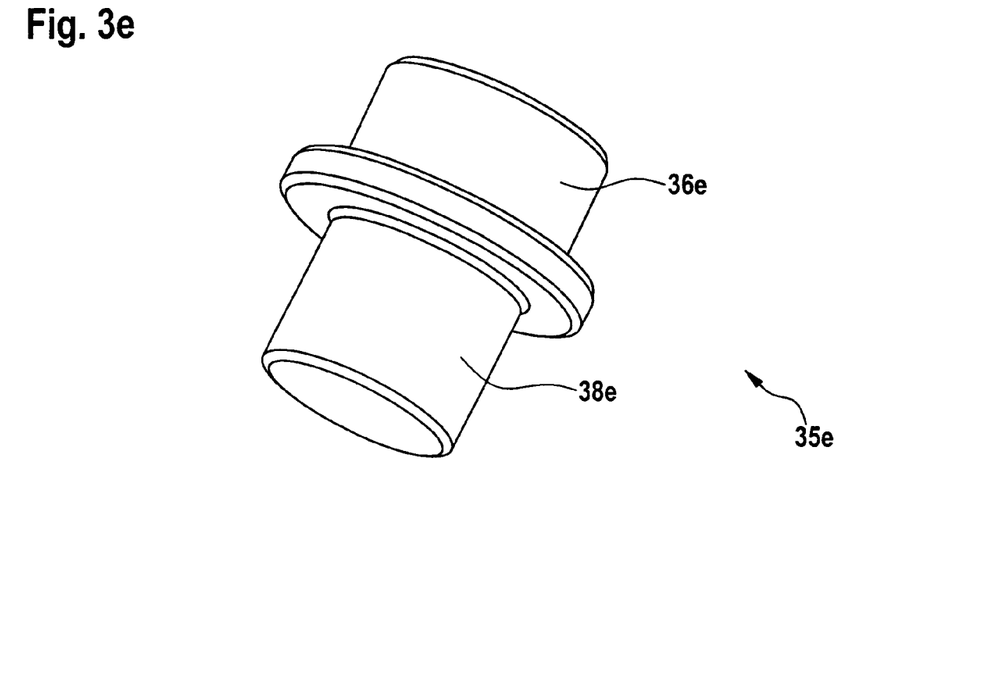

In the insert part 35e, the shoe 38e has a smaller outer circumference than the plug element 36e.

Figure 3F:
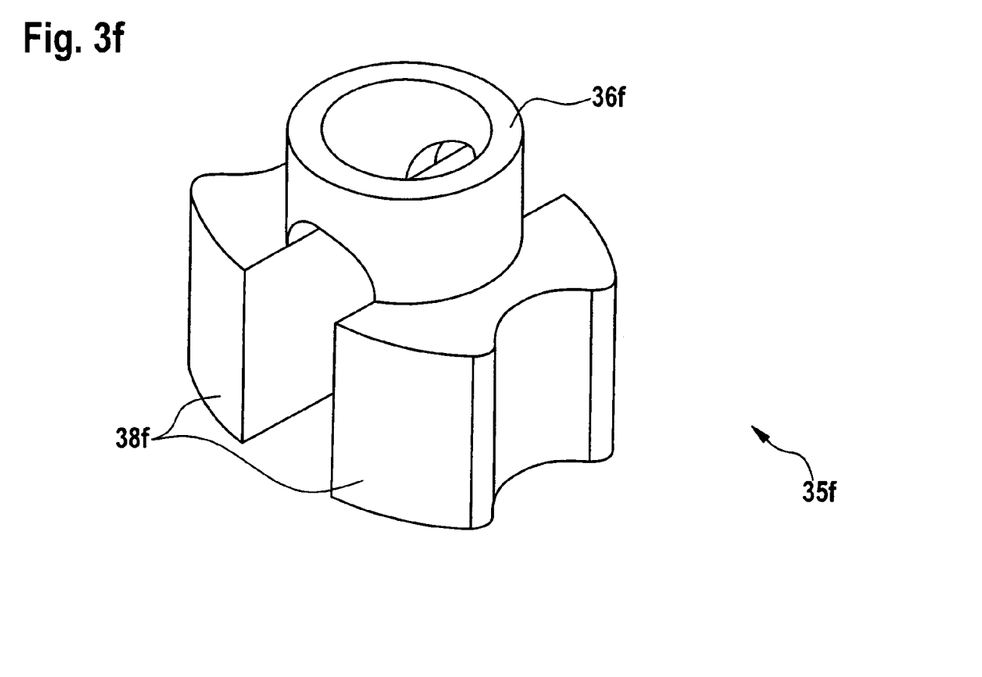

The insert part 35f, finally, comprises a hollow cylindrical plug element 36f, and a shoe 38f which, on its outer circumference, has radially inwardly extending recesses.

In addition to the embodiments shown in the figures of the drawing, many other geometric configurations of the insert part according to the invention are also possible, for example the above-described variant in which the outer circumference of the shoe has radially outwardly protruding stabilizer wings. It is thus possible to cover practically all conceivable individual situations arising in the area of the footplate of a patient's stirrup bone.

The invention claimed is:

1. A middle ear prosthesis for total reconstruction of an ossicular chain in humans comprising: a shaft-like prosthesis body, a first coupling element at a first end of the shaft-like prosthesis body and designed either as a head plate for mechanical connection of the prosthesis to a tympanic membrane or as a clip for coupling the prosthesis to a manubrium, and a second coupling element at a second end of the shaft-like prosthesis body and for mechanical connection of the prosthesis to a footplate of a stirrup, the second coupling element having a receiving part connected rigidly to the shaft-like prosthesis body and an insert part, with the insert part having a plug element that can be inserted into the receiving part coaxially with respect to a longitudinal axis of the shaft-like prosthesis body and a shoe that is connected rigidly to the plug element for bearing on the footplate of the stirrup in an implanted state of the prosthesis, wherein the shoe has a stamp-shaped structure and an end portion of the shoe for bearing on the footplate of the stirrup in the implanted state of the prosthesis has a surface curved concavely in a direction of the plug element, wherein the receiving part, at an end thereof directed away from the shaft-like prosthesis body, has a receiving opening designed as an elongate cavity with a cylindrical bore which extends in an axial direction of the prosthesis body and encloses a full circumference of the plug element of the insert part in an assembled state, wherein an inside diameter of the elongate cavity is greater than a maximum transverse extent of the plug element transverse to the longitudinal axis of the shaft-like prosthesis body, wherein the elongate cavity is closed at an end directed away from the insert part and, in the assembled state, acts as an end abutment for the plug element, and wherein the second coupling element extends, in the axial direction of the prosthesis body, by at most a third of an axial length of the prosthesis body.

2. The middle ear prosthesis according to claim 1, wherein the second coupling element extends, in the axial direction of the prosthesis body, by at most a quarter of the axial length of the prosthesis body.

3. The middle ear prosthesis according to claim 1, wherein the insert part is actively wedged into the receiving part at selectable discrete relative coaxial positions along an axial extent by an external action on the insert part and/or on the receiving part.

4. The middle ear prosthesis according to claim 3, wherein the insert part is actively wedged into the receiving part by the action of an external mechanical force acting in a radial direction on the receiving part.

5. The middle ear prosthesis according to claim 3, wherein the insert part is actively wedged into the receiving part by external application of heat to the middle ear prosthesis.

6. The middle ear prosthesis according to claim 5, wherein the insert part and/or the receiving part are made completely or partially of a material with shape memory.

7. The middle ear prosthesis according to claim 1, wherein the plug element has a continuously cylindrical shape.

8. The middle ear prosthesis according to claim 1, wherein the plug element, at a axial end thereof directed toward the receiving part in the assembled state, has a thickened area in a shape of an ellipsoid.

9. The middle ear prosthesis according to claim 8, wherein the second coupling element is designed as a ball joint.

10. The middle ear prosthesis according to claim 1, wherein the receiving part has a cylindrical outer contour in cross section taken in a direction perpendicular to the longitudinal axis.

11. The middle ear prosthesis according to claim 1, wherein the prosthesis body has at least one joint.

12. The middle ear prosthesis according to claim 1, wherein the middle ear prosthesis or parts thereof are made of biocompatible plastics and/or of composite fiber materials and/or of titanium and/or gold and/or tantalum and/or of an alloy of said metals and/or of a material with shape memory.

13. The middle ear prosthesis according to claim 1, wherein, before being inserted into the receiving part, the insert part is stored in a sterile package.

14. The middle ear prosthesis according to claim 1, wherein, after the plug element has been inserted as far as the end abutment into the cavity of the receiving part, the overall length of the middle ear prosthesis is between 0.3 and 0.8 mm.

15. The middle ear prosthesis of claim 1, wherein a total length of the middle ear prosthesis is fixed once the plug element of the insert part is inserted into the cavity of the receiving part.

16. A middle ear prosthesis for total reconstruction of an ossicular chain in humans, the middle ear prosthesis comprising:
a shaft-like prosthesis body;
a first coupling element connected to a first end of the shaft-like prosthesis body, the first coupling element being designed either as a head plate for mechanical connection of the middle ear prosthesis to a tympanic membrane or as a clip for coupling the middle ear prosthesis to a manubrium; and
a second coupling element connected to a second end of the shaft-like prosthesis body, the second coupling element being for mechanical connection of the middle ear prosthesis to a footplate of a stirrup, the second coupling element having a receiving part rigidly connected to the shaft-like prosthesis body and an insert part, the insert part including a plug element inserted into the receiving part coaxially with respect to a longitudinal axis of the shaft-like prosthesis body and a shoe rigidly connected to the plug element, with the shoe for bearing on the footplate of the stirrup in an implanted state of the middle ear prosthesis;
wherein the shoe has a plate-shaped structure and an end portion of the shoe for bearing on the footplate of the stirrup in the implanted state of the middle ear prosthesis has a surface curved concavely in a direction of the plug element;
wherein the receiving part has an away end distal from the shaft-like prosthesis body, the away end including a receiving opening designed as an elongate cavity with a bore which extends in an axial direction of the shaft-like prosthesis body and encloses a full circumference of the plug element of the insert part in an assembled state;
wherein an inside diameter of the elongate cavity is greater than a maximum transverse extent of the plug element transverse to the longitudinal axis of the shaft-like prosthesis body;
wherein the elongate cavity is closed at a distal end directed away from the insert part and, in the assembled state, acts as an end abutment for the plug element; and
wherein the second coupling element extends in the axial direction of the shaft-like prosthesis body by at most a third of an axial length of the shaft-like prosthesis body.

17. The middle ear prosthesis of claim 16, wherein a total length of the middle ear prosthesis is fixed once the plug element of the insert part is inserted into the cavity of the receiving part.

18. A middle ear prosthesis kit for forming a middle ear prosthesis for total reconstruction of an ossicular chain in humans, the middle ear prosthesis kit comprising:
a shaft-like prosthesis body;
a first coupling element connected to a first end of the shaft-like prosthesis body, the first coupling element being designed either as a head plate for mechanical connection of the middle ear prosthesis to a tympanic membrane or as a clip for coupling the middle ear prosthesis to a manubrium; and
a second coupling element connected to a second end of the shaft-like prosthesis body, the second coupling element being for mechanical connection of the middle ear prosthesis to a footplate of a stirrup, the second coupling element having a receiving part rigidly connected to the shaft-like prosthesis body and one of a plurality of insert parts, each insert part having a plug element that can be inserted into the receiving part coaxially with respect to a longitudinal axis of the shaft-like prosthesis body and a shoe connected to the plug element, with the shoe for bearing on the footplate of the stirrup in an implanted state of the middle ear prosthesis;

wherein the shoe has a stamp-shaped structure and an end portion of the shoe for bearing on the footplate of the stirrup in the implanted state of the middle ear prosthesis has a surface curved concavely in a direction of the plug element;

wherein the receiving part has an away end distal from the shaft-like prosthesis body, the away end including a receiving opening designed as an elongate cavity with a cylindrical bore which extends in an axial direction of the shaft-like prosthesis body and encloses a full circumference of the plug element of the insert part in an assembled state;

wherein an inside diameter of the elongate cavity is greater than a maximum transverse extent of the plug element transverse to the longitudinal axis of the shaft-like prosthesis body;

wherein the elongate cavity is closed at a distal end directed away from the insert part and, in the assembled state, acts as an end abutment for the plug element; and wherein the second coupling element extends in the axial direction of the shaft-like prosthesis body by at most a third of an axial length of the shaft-like prosthesis body;

wherein the insert parts are each different but are designed in such a way that the middle ear prosthesis has a same axial overall length after the plug element of each one of a selected one of the insert parts has been inserted as far as the end abutment into the elongate cavity of the receiving part.

19. The middle ear prosthesis of claim 18, wherein a total length of the middle ear prosthesis is fixed once the plug element of the insert part is inserted into the cavity of the receiving part.

\* \* \* \* \*